(12) United States Patent
Haraguchi (10) Patent No.: US 11,628,026 B2
(45) Date of Patent: Apr. 18, 2023

(54) JOINT RING AND MEDICAL MANIPULATOR

(71) Applicant: OLYMPUS CORPORATION, Tokyo (JP)

(72) Inventor: Masafumi Haraguchi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 1542 days.

(21) Appl. No.: 15/824,302

(22) Filed: Nov. 28, 2017

(65) Prior Publication Data

US 2018/0078322 A1 Mar. 22, 2018

Related U.S. Application Data

(63) Continuation of application No. PCT/JP2016/066007, filed on May 31, 2016.

(30) Foreign Application Priority Data

Jun. 16, 2015 (JP) .............................. JP2015-121148

(51) Int. Cl.
*A61B 1/00* (2006.01)
*A61B 1/008* (2006.01)
(Continued)

(52) U.S. Cl.
CPC .............. *A61B 34/70* (2016.02); *A61B 1/008* (2013.01); *A61B 1/0011* (2013.01);
(Continued)

(58) Field of Classification Search
CPC ..... A61B 34/70; A61B 1/0011; A61B 1/0055; A61B 1/008; A61B 17/00234;
(Continued)

(56) References Cited

U.S. PATENT DOCUMENTS 3,190,286 A * 6/1965 Stokes ..................... B25J 18/06
600/179
4,700,693 A 10/1987 Lia et al.
(Continued)

FOREIGN PATENT DOCUMENTS

EP 0754429 A2 1/1997
JP S49-29114 Y 8/1974
(Continued)

OTHER PUBLICATIONS

International Search Report dated Aug. 16, 2016 issued in PCT/JP2016/066007.
(Continued)

*Primary Examiner* — Gary Jackson
*Assistant Examiner* — Sebastian X Lukjan
(74) *Attorney, Agent, or Firm* — Scully, Scott, Murphy & Presser, P.C.

(57) ABSTRACT

A joint ring includes a main body part and a pair of protrusion parts protruding from a first surface of the main body part in a direction of a central axis thereof and having spherical surfaces on protruding portions. The main body part includes a pair of engagement holes and a pair of receiving holes. The protrusion parts include engagement parts which are configured to be capable of being inserted into the engagement holes. When the joint rings are arranged in the direction of the central axis and the protrusion parts of a first joint ring enter the receiving holes of a second joint ring, the spherical surfaces come into contact with receiving surfaces inside the receiving holes, and the first joint ring and the second joint ring become rotatable relative to each other with a line segment connecting centers of the respective spherical surfaces as a rotational center.

6 Claims, 6 Drawing Sheets

(51) Int. Cl.
  *A61B 1/005* (2006.01)
  *A61B 17/00* (2006.01)
  *A61B 34/00* (2016.01)
  *B25J 9/06* (2006.01)
  *F16H 19/06* (2006.01)
(52) U.S. Cl.
  CPC ...... *A61B 1/0055* (2013.01); *A61B 17/00234* (2013.01); *A61B 34/71* (2016.02); *B25J 9/065* (2013.01); *A61B 1/00073* (2013.01); *A61B 2017/00314* (2013.01); *A61B 2017/00327* (2013.01); *A61B 2017/00477* (2013.01); *F16H 19/06* (2013.01); *F16H 2019/0695* (2013.01)
(58) Field of Classification Search
  CPC ................ A61B 34/71; A61B 1/00073; A61B 2017/00314; A61B 2017/00327; A61B 2017/00477; B25J 9/065; F16H 19/06; F16H 2019/0695
  See application file for complete search history.

(56) References Cited

U.S. PATENT DOCUMENTS

| | | | | |
|---|---|---|---|---|
| 4,790,294 A | * | 12/1988 | Allred, III | ........... A61B 1/0055 600/149 |
| 4,796,607 A | | 1/1989 | Allred, III et al. | |
| 2010/0261971 A1 | * | 10/2010 | Danitz | ..................... B25J 9/104 600/204 |
| 2010/0262162 A1 | | 10/2010 | Omori | |
| 2012/0289946 A1 | * | 11/2012 | Steger | ..................... A61B 34/30 606/1 |
| 2014/0135685 A1 | | 5/2014 | Kabe et al. | |
| 2014/0316432 A1 | | 10/2014 | Malkowski | |
| 2014/0378767 A1 | * | 12/2014 | Lee | ........................ A61B 1/005 600/141 |

FOREIGN PATENT DOCUMENTS

| | | |
|---|---|---|
| JP | S51-060688 U1 | 5/1976 |
| JP | S53-105493 U | 8/1978 |
| JP | H01-178228 A | 7/1989 |
| JP | H03-162817 A | 7/1991 |
| JP | H09-000525 A | 1/1997 |
| JP | 2000-296103 A | 10/2000 |
| WO | 2015/079809 A1 | 6/2015 |

OTHER PUBLICATIONS

Japanese Office Action dated May 16, 2017 issued in JP 2017-513834.
Extended Supplementary European Search Report dated Jan. 9, 2019 in European Patent Application No. 16 81 1415.5.

* cited by examiner

JOINT RING AND MEDICAL MANIPULATOR

This application is a continuation application based on PCT Patent Application No. PCT/JP2016/066007, filed May 31, 2016, claiming priority based on Japanese Patent Application No. 2015-121148, filed Jun. 16, 2015, the content of which is incorporated herein by reference.

BACKGROUND OF THE INVENTION

Field of the Invention

The present invention relates to a joint ring, and particularly relates to a joint ring constituting a bending section of a medical manipulator and a medical manipulator using the joint ring.

Description of the Related Art

In laparoscopic surgery, it is necessary to treat and observe affected portion from limited access routes. For this reason, the degree of freedom of laparoscopic surgery is limited and the difficulty level of a procedure is increased in comparison to laparotomy surgery, but merits of patients are great in view of postoperative recovery and the like.

Treatment and observation having a high degree of freedom are possible using a medical manipulator having a bendable mechanism on distal end thereof. As one bendable mechanism of a medical manipulator, a structure (hereinafter referred to as a "joint ring structure") in which a plurality of joint rings or bending pieces formed in annular shapes are arranged in a direction of an axis, as illustrated in Japanese Unexamined Patent Application, First Publication No. 2000-296103, is known.

Solution to Problem

According to a first aspect of the present invention, a joint ring which constitutes a bending section of a medical manipulator, the joint ring includes: a main body part formed in an annular shape; and a pair of protrusion parts protruding from a first surface of the main body part in a direction of a central axis thereof and having spherical surfaces on protruding portions, wherein the main body part includes: a pair of engagement holes formed to oppose each other across the central axis, and a pair of receiving holes which are open in a second surface in the direction of the central axis, have sizes such that the spherical surfaces are configured to be capable of entering the receiving holes, and are formed to oppose each other across the central axis, the pair of protrusion parts include engagement parts which are configured to be capable of being inserted into the engagement holes, and are engaged and fixed to the main body part so that the spherical surfaces protrude toward the first surface side of the main body part by inserting the engagement parts into the engagement holes, and when a plurality of the joint rings are arranged in the direction of the central axis and the pair of protrusion parts of a first joint ring enter the pair of receiving holes of a second joint ring adjacent to the first joint ring, the spherical surfaces of the first joint ring come into contact with receiving surfaces inside the receiving holes of the second joint ring, and the first joint ring and the second joint ring become rotatable relative to each other with a line segment connecting centers of the respective spherical surfaces of the pair of protrusion parts of the first joint ring as a rotational center.

According to a second aspect of the present invention, in the joint ring according to the first aspect, the pair of protrusion parts and the pair of receiving holes may be provided to be shifted in phase by 90 degrees around the central axis.

According to a third aspect of the present invention, in the joint ring according to the first or second aspects, the protrusion part may have a through hole extending to be parallel to the central axis. The pair of receiving holes may be formed to pass through the main body part to be parallel to the central axis.

According to a fourth aspect of the present invention, in the joint ring according to the third aspect, a diameter of the through hole may gradually increase toward both ends thereof in the direction of the central axis. Diameters of the pair of receiving holes may gradually increase toward both ends thereof in the direction of the central axis.

According to a fifth aspect of the present invention, in the joint ring according to any one of the first to fourth aspects, the pair of protrusion parts may be formed of a harder material than a material of the main body part.

According to a sixth aspect of the present invention, a medical manipulator includes the bending section constituted using a plurality of the joint rings according to any one of the first to fifth aspects.

Advantageous Effects of Invention

According to the above-described joint ring, a bendable mechanism in which tilting stability of a joint ring or the like is kept high is capable of being configured.

According to the above-described medical manipulator, a configuration in which tilting stability of a joint ring or the like is kept high is capable of being obtained.

DETAILED DESCRIPTION OF THE PREFERRED EMBODIMENTS

An embodiment of the present invention will be described below with reference to FIGS. 1 to 7.

Figure 1:
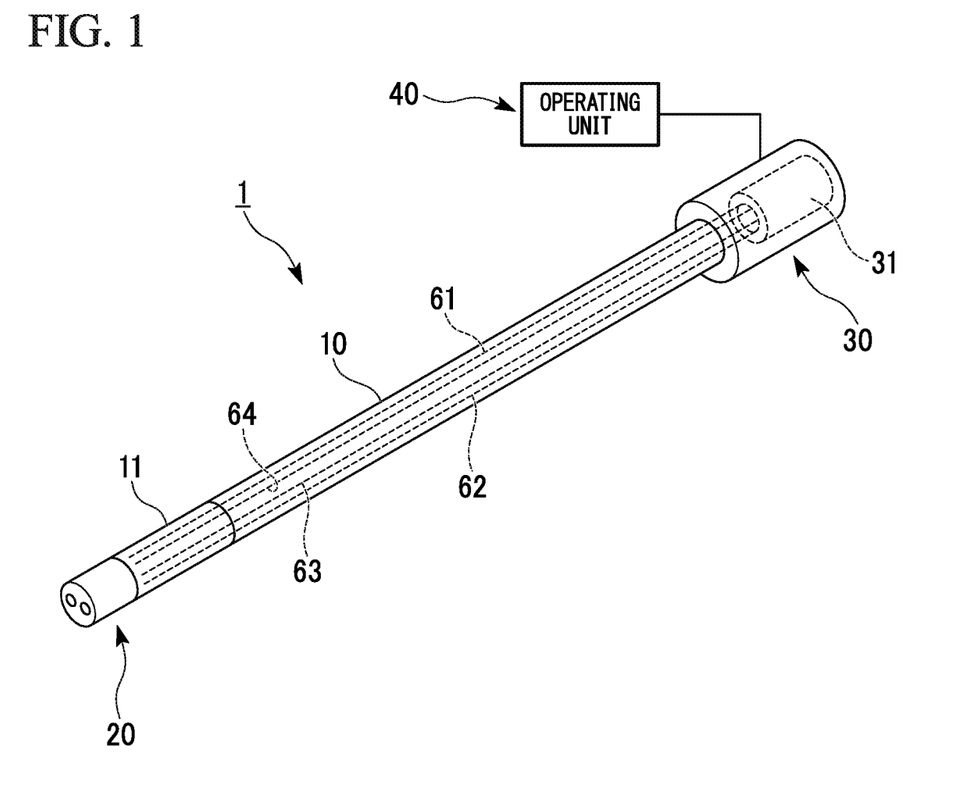
FIG. 1 is an overall view of an endoscope according to an embodiment of the present invention.

FIG. 1 is a diagram illustrating an endoscope 1 serving as a medical manipulator according to an embodiment. In laparoscopic surgery or the like, the endoscope 1 is inserted into a body cavity via a trocar or the like and used. The endoscope 1 includes an insertion section 10 having a bending section 11 to be bendable, an observation section (an end effector) 20 attached to a distal end portion of the insertion section 10, a drive section 30 attached to a proximal end portion of the insertion section 10, and an operating unit 40 configured to operate the drive section 30.

The insertion section 10 is formed in a tubular shape with a metal or the like. The bending section 11 has a structure in which a plurality of joint rings are disposed to be arranged in a direction of an axis thereof. Although details of a structure of the bending section 11 will be described below, the most distal end side joint ring and the drive section 30 are connected by a first pair of wires (power transmission members) 61 and 62 and a second pair of wires 63 and 64 inserted into the insertion section 10. The bending section 11 is capable of being subject to a bending operation with two degrees of freedom which bends the bending section 11 in four directions away from the axis by advancing and retracting the wires 61 to 64 using a drive force generated by the drive section 30.

The observation section 20 has a known structure including an imaging unit including a solid-state imaging device or the like and a lighting unit including a light emitting diode (LED), a light guide connected to a light source, or the like. An image acquired by the observation section 20 is displayed on an external monitor or the like (not shown) connected to the endoscope 1 through a wiring or the like passing through the insertion section 10.

The drive section 30 includes a drive force generation section 31 configured to generate a drive force. The drive force generation section 31 includes a plurality of drive mechanisms such as motors. The first pair of wires 61 and 62 and the second pair of wires 63 and 64 are connected to different drive mechanisms. The drive mechanisms and the wires may be directly connected or may be connected via gears for deceleration or the like.

There are no particular restrictions on a specific constitution, a position to be provided, and the like of the operating unit 40, and a structure or the like of a known operating unit is capable of being appropriately selected and used as long as the operating unit 40 is configured to be able to operate the drive section 30.

Figure 2:
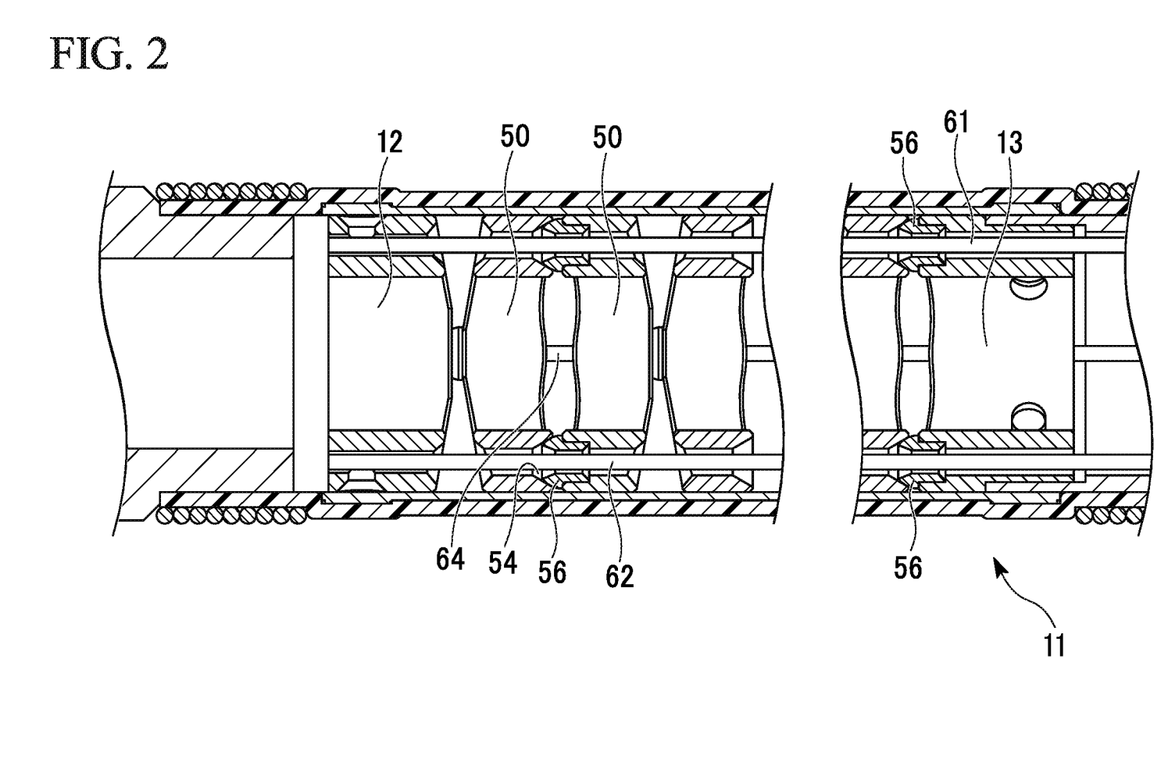
FIG. 2 is a cross-sectional view of a bending section of the endoscope.

FIG. 2 is a cross-sectional view of the bending section 11. The bending section 11 is constituted using three types of joint rings, i.e., a distal end side joint ring 12 connected to the wires 61 to 64, a proximal end side joint ring 13 disposed on a proximal end side of the bending section 11, and a plurality of basic joint rings 50 disposed between the distal end side joint ring 12 and the proximal end side joint ring 13. All of the three types of joint rings are formed in annular shapes, and the wires 61 to 64 are inserted into the joint rings in a state in which the three types of joint rings are disposed to be arranged in the direction of the axis in an order of the distal end side joint ring 12, the plurality of basic joint rings 50, and the proximal end side joint ring 13 from a distal end side of the bending section 11.

Figure 3:
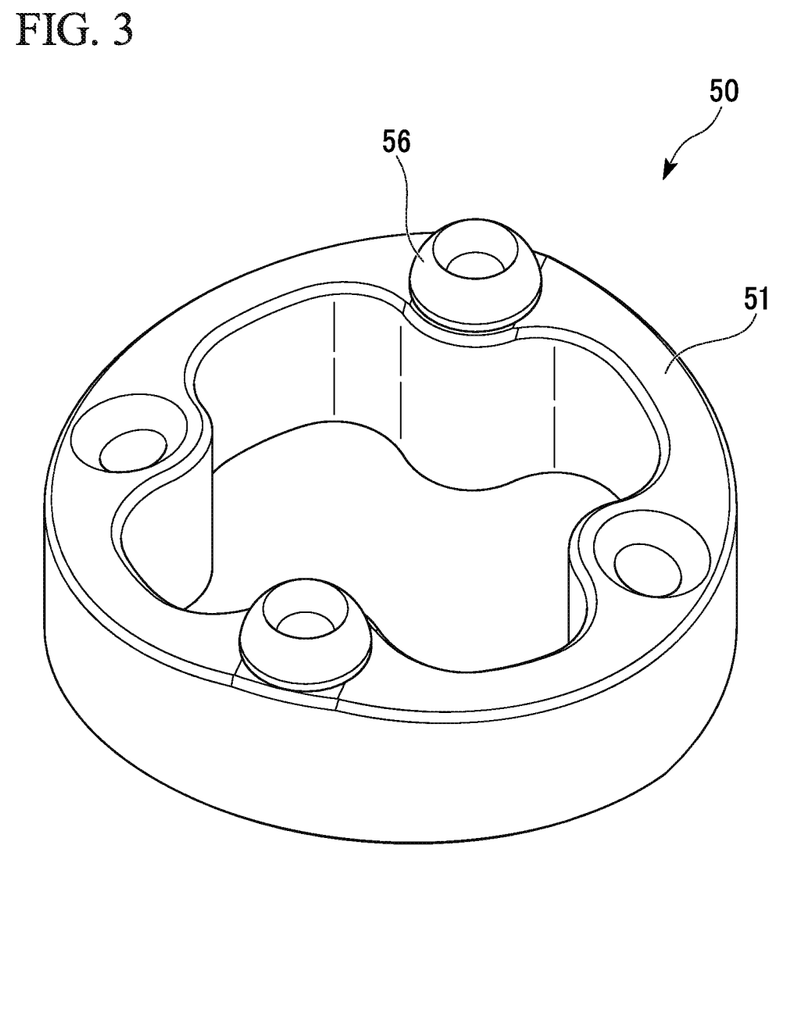
FIG. 3 is a perspective view of a basic joint ring.

FIG. 3 is a perspective view illustrating the basic joint ring 50. The basic joint ring 50 is a joint ring in the embodiment and includes an annular main body part 51 and a pair of protrusion parts 56 attached to the main body part 51.

Figure 4:
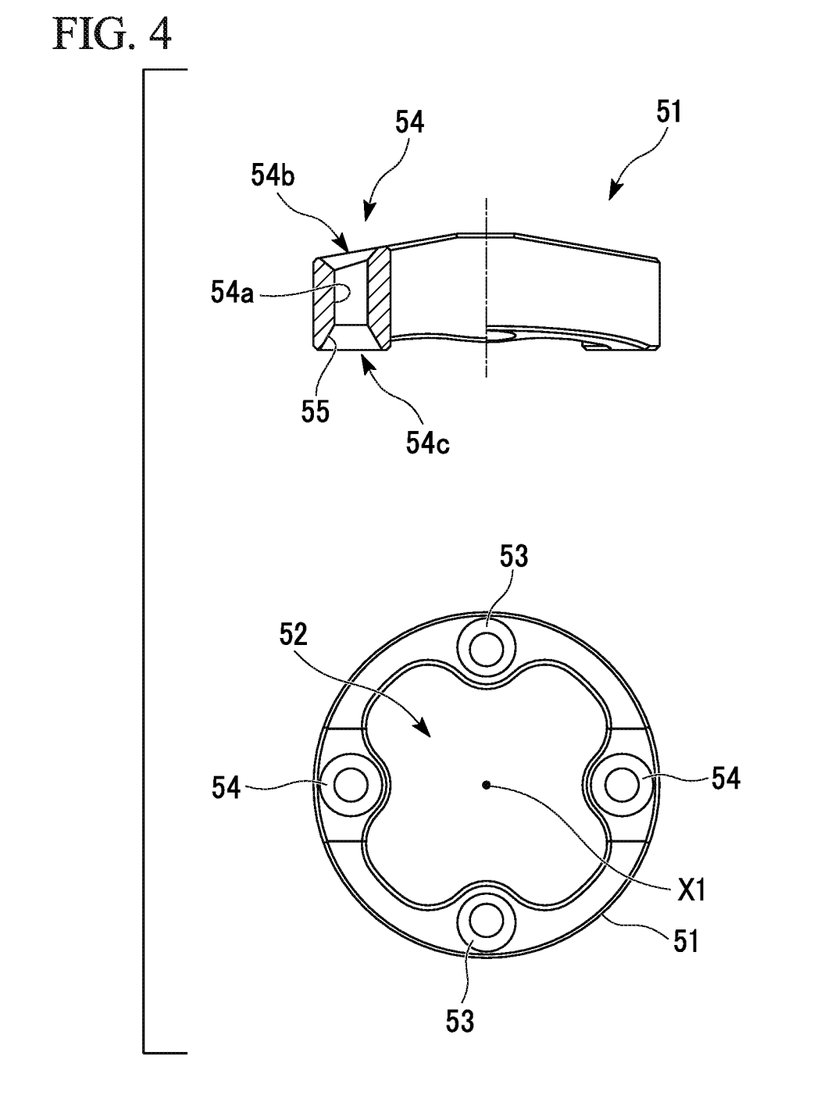
FIG. 4 is a diagram illustrating a shape of a main body part constituting the basic joint ring.

A lower part of FIG. 4 is a front view of the main body part 51, and an upper part thereof is a cross-sectional view of the main body part 51. The main body part 51 is formed in an annular shape with, for example, a metal such as stainless steel. The main body part 51 has a containing hole 52 through which an inner object such as a wiring or a light guide of the observation section 20 and a tube used as a treatment instrument channel passes in a center thereof.

Four through holes extending in a direction of a central axis X1 (hereinafter simply referred to as an "axis X1" in some cases) of the main body part 51 are provided around the containing hole 52. Two of the four through holes are engagement holes 53 to which the protrusion parts 56 are attached, and the other two holes are a pair of receiving holes 54 in which the protrusion parts 56 enter from a back surface (a second surface) side when the plurality of basic joint rings 50 are arranged in the direction of the central axis X1 of the main body part 51.

The engagement holes 53 and the receiving holes 54 are alternately disposed at equal intervals around the axis X1. Therefore, in the engagement holes 53 and the receiving holes 54, any neighboring through holes have a positional relationship with in which the through holes are separated from each other by 90 degrees as a rotational angle around the axis X1, and both a line connecting centers of the two engagement holes 53 and a line connecting centers of the two receiving holes 54 pass through the axis X1. In other words, the two engagement holes 53 oppose each other across the central axis X1 and the two receiving holes 54 oppose each other across the central axis X1.

FIG. 4 illustrates a cross-sectional shape of the receiving hole 54. An intermediate part 54a in the direction of the axis X1 has a cylindrical space having a constant inner diameter. A first enlarged diameter part 54b on a front surface side has a shape with a diameter which gradually increases toward a front surface of the main body part 51. A second enlarged diameter part 54c on a back surface side has a shape with a diameter which gradually increases toward a back surface of the main body part 51. The second enlarged diameter part 54c has a circular truncated cone-shaped space having an axis which is parallel to the axis X1. A tapered inner surface of the second enlarged diameter part 54c is a receiving surface 55 coming into contact with the protrusion part 56.

Figure 5:
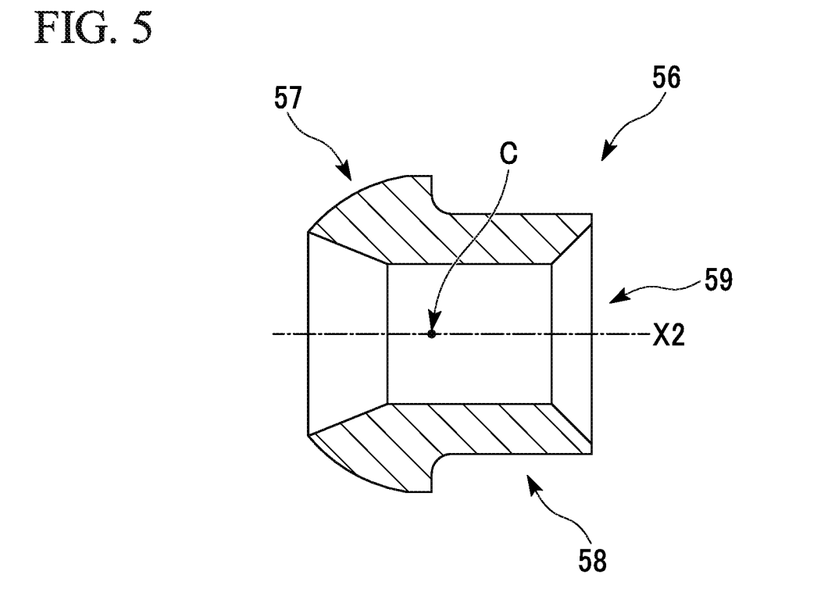
FIG. 5 is a cross-sectional view illustrating a protrusion part constituting the basic joint ring.

FIG. 5 is a cross-sectional view illustrating the protrusion part 56. The protrusion part 56 includes a hemispherical distal end part 57 and a substantially cylindrical engagement part 58 connected to the distal end part 57. A distal end side surface of the distal end part 57 is a spherical surface and a center C of a sphere having the spherical surface is located on an axis X2 of the engagement part 58. A through hole 59 having the axis X2 as a central axis thereof is provided in the protrusion part 56. Both end portions of the through hole 59 are formed in tapered shapes with diameters which gradually increase toward a distal end and a proximal end thereof, respectively.

The protrusion part 56 is engaged and fixed to the main body part 51 to protrude toward a front surface (a first surface) side of the main body part 51 by inserting the engagement part 58 into the engagement hole 53 from the front surface side of the main body part 51. As a material for forming the protrusion part 56, a metal is desirable. Examples of the material include brass, titanium, a martensite-based stainless steel such as SUS420 J2 (a JIS standard), materials obtained by performing coating on various stainless steels, or the like.

As shown in FIG. 2, the basic joint rings 50 are disposed such that phases of the protrusion parts 56 in the neighboring basic joint rings 50 differ by 90 degrees as a rotational angle around the axis X1 in a state in which the protrusion parts 56 face the distal end side joint ring 12 side. Thus, in two neighboring basic joint rings 50, the receiving hole 54 of the basic joint ring 50 located on the distal end side is located in front of the protrusion part 56 of the basic joint ring 50 located on the proximal end side. Moreover, as enlarged and shown in FIG. 6, the distal end part 57 of the basic joint ring 50 on the proximal end side enters the second enlarged diameter part 54c of the basic joint ring 50 on the distal end side, and the spherical surface of the distal end part 57 comes into contact with the receiving surface 55.

Although not shown in the cross section of FIG. 2, a concave part having the same shape as the second enlarged diameter part 54c is provided in a back surface of the distal end side joint ring 12, and the protrusion part 56 of the basic joint ring 50 located on the most distal end side enters the concave part in the same manner as above. As shown in FIG. 2, the two protrusion parts 56 are attached to a front surface of the proximal end side joint ring 13. The protrusion part 56 of the proximal end side joint ring 13 enters the second enlarged diameter part 54c of the basic joint ring 50 located on the most proximal end side like the protrusion part attached to the basic joint ring 50.

The four wires 61 to 64 are respectively inserted into the four through holes of the basic joint ring 50 in a state in which the three types of joint rings have the above-described positional relationship such that the bending section 11 is constituted.

An operation in which the endoscope 1 according to the embodiment configured as described above is used will be described.

A user operates the operating unit 40 to drive the drive section 30 and perform the bending operation on the bending section 11. The first pair of wires 61 and 62 and the second pair of wires 63 and 64 are advanced and retracted with respect to the insertion section 10 by the drive mechanism of the drive section 30. Since distal ends of the wires 61 to 64 are connected and fixed to the distal end side joint ring 12, the bending section 11 bends toward a phase of the through hole through which the wire driven to retract with respect to the insertion section 10 is inserted.

When the bending section 11 bends, each joint ring constituting the bending section 11 rotates relative to a neighboring joint ring. Such relative rotation will be described with reference to FIGS. 6 and 7. Note that, in FIGS. 6 and 7, the inserted wire will be omitted for the sake of ease of viewing.

Figure 6:
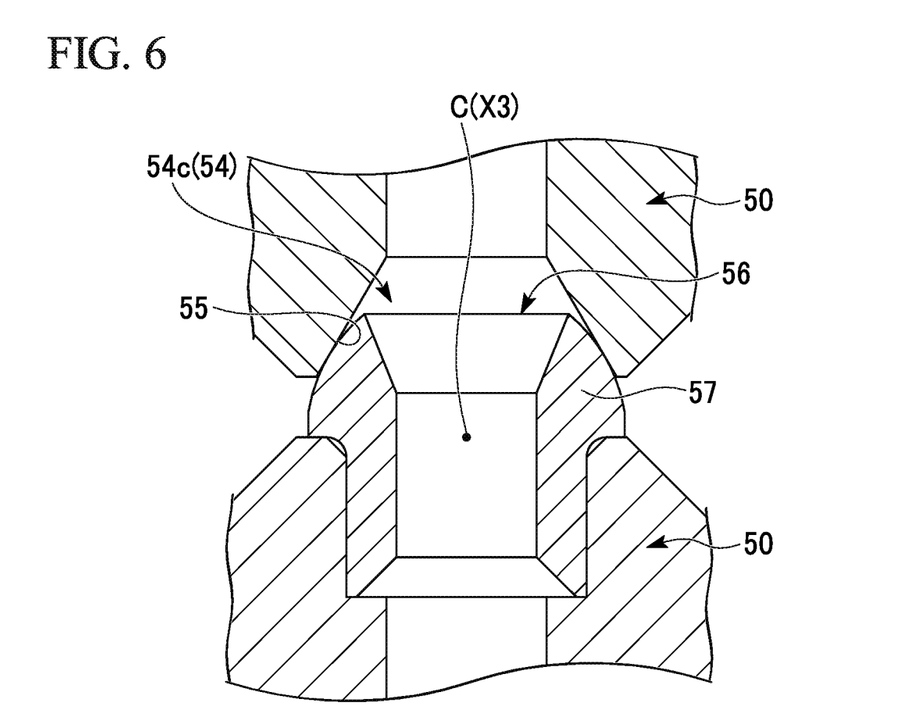
FIG. 6 is an enlarged diagram illustrating a protrusion part and a receiving hole of neighboring basic joint rings.

Two neighboring basic joint rings 50 are mutually supported at two positions when the two protrusion parts 56 enter the two receiving holes 54. FIG. 6 illustrates a state in which the neighboring basic joint rings 50 are arranged in a straight line, that is, the central axes X1 (not shown in FIG. 6) of the two basic joint rings 50 coincide. When the wire is operated in this state, one of the basic joint rings 50 rotates relative to the other of the basic joint rings 50. At this time, a central axis (a rotational axis) X3 of the relative rotation is a line segment connecting centers C of spherical surface shapes of distal end parts 57 in the two protrusion parts 56. Since the two protrusion parts 56 are separated from each other by 180 degrees as a rotational angle around the central axis X1, the rotational axis X3 intersects the central axis X1 of the basic joint ring on the proximal end side.

Figure 7:
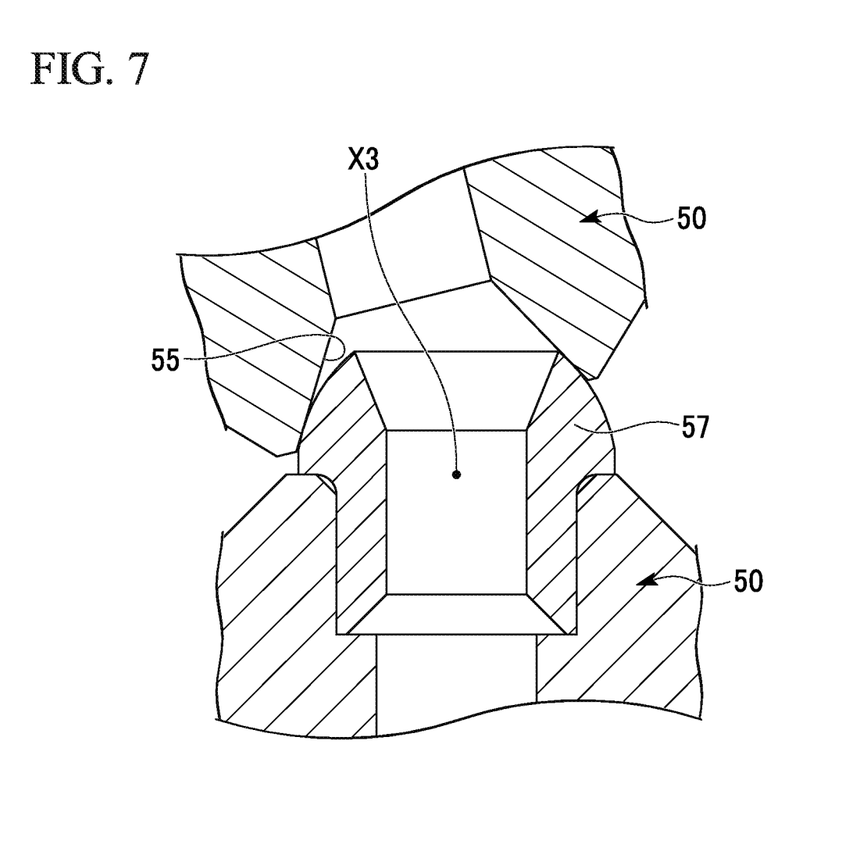
FIG. 7 is an enlarged diagram illustrating a protrusion part and a receiving hole when neighboring basic joint rings relatively rotate.

Since the protrusion part 56 and the receiving hole 54 come into contact with each other at the spherical surface of the distal end part 57 and the tapered receiving surface 55, the protrusion part 56 and the receiving hole 54 come into linear contact with each other in a circular arc shape. For this reason, when the two neighboring basic joint rings 50 rotate relative to each other as shown in FIG. 7, there is no room to rotate relatively around the central axis X1, and thus there is no shaking around the central axis X1. Furthermore, the receiving surface 55 relatively moves to slide on the spherical surface of the distal end part 57 at a time of relative rotation, but the center of such relative movement is always the rotational axis X3, and thus no shaking of the rotational axis occurs.

With the above-described action, when the bending section 11 bends, neighboring basic joint rings 50 perform relative rotation substantially as designed, and almost no errors occur. Since the distal end side joint ring 12 and the proximal end side joint ring 13 also come into contact with neighboring basic joint rings 50 at the spherical surface of the protrusion part 56 and the receiving surface 55, the same effects as described above are capable of being obtained.

As described above, according to the endoscope 1 of the embodiment, in a plurality of joint rings constituting the bending section 11 serving as a bendable mechanism, two neighboring basic joint rings 50 are disposed such that the spherical surfaces of the two protrusion parts 56 provided on one of the two neighboring basic joint rings 50 come into contact with the two receiving surfaces 55 provided on the other of the two neighboring basic joint rings 50. For this reason, the two neighboring basic joint rings 50 rotate relative to each other while always using the predetermined rotational axis X3 as a center. Therefore, tilting stability of the joint ring when the bending section 11 bends is kept high, and thus drive control is capable of being performed with high precision, while the endoscope 1 has a joint ring structure.

Also, since all of the receiving holes 54 and the through holes 59 of the protrusion parts 56 into which the wires 61 to 64 are inserted have diameters which gradually increase toward both ends thereof, the inserted wires 61 to 64 are capable of bending along enlarged-diameter inner surfaces even when neighboring basic joint rings 50 tilt. Therefore, it is possible to suppress situations such as the wire being in contact with an edge of the through hole and being damaged.

A position at which the receiving surface 55 and the spherical surface of the protrusion part 56 come into contact with each other is capable of being appropriately set in the embodiment. However, when a contact place is too close to an end portion of the receiving hole 54, the protrusion part 56 may come off the receiving hole 54 at a time of relative rotation. Conversely, when the contact place is too far from the end portion of the receiving hole 54, the end portion (an edge) of the receiving hole 54 or an end portion (an edge) of the through hole 59 may damage or shear the wires 61 to 64. Therefore, when the receiving surface comes into contact with the spherical surface of the protrusion part, it is desirable to set a size of the protrusion part, an inclination angle of the receiving surface, or the like such that about 40% or more and about 60% or less of the distal end part having the spherical surface is located in the receiving hole.

Although the embodiment of the present invention has been described above, the technical scope of the present invention is not limited to the above-described embodiment, and a change in a combination of the constituent elements, an addition of various modifications to the constituent elements, or a deletion of the constituent elements is possible without departing from the gist of the present invention.

For example, although a case in which the main body part and the protrusion part constituting the basic joint ring are separate members has been described in the above-described embodiment, the main body part and the protrusion part may be integrally formed with a single member in place of this.

Here, when the main body part and the protrusion part are separate members, there are merits in that materials thereof are appropriately selected so that the sliding of the main body part and the protrusion part when the main body part and the protrusion part slide is capable of being improved or the protrusion part is not easily deformed when the protrusion part is formed of a harder material than a material of the main body part, and thus behaviors of the joint rings at a time of relative rotation are capable of being further stabilized.

Also, although a case in which the power transmission member is inserted into the protrusion part and the receiving hole has been described in the above-described embodiment, the power transmission member may be inserted into another place of the joint ring. For example, the power transmission member may be inserted into a through hole for the power transmission member formed at a position which is 45 degrees as a rotational angle away from the protrusion part or the receiving hole.

In addition, although a case in which the protrusion part provided on the joint ring on the proximal end side enters the receiving hole provided in the joint ring on the distal end side has been described in the above-described embodiment, the protrusion part provided on the joint ring on the distal end side may be configured to enter the receiving hole provided in the joint ring on the proximal end side in place of this. In the above-described embodiment, such a constitution is capable of being realized by reversing the disposition while maintaining the arrangement of the joint rings, that is, by setting the distal end side joint ring 12 to the proximal end side and the proximal end side joint ring 13 to the distal end side. In this case as well, a rotational axis when neighboring joint rings rotate relative to each other is made substantially immovable, and thus the same effects are capable of being obtained. Therefore, any constitution may be adopted in consideration of a procedure or the like of assembling a bendable mechanism.

In addition, although a constitution case which includes the two pair of wires and is capable of bending in four directions has been described in the above-described embodiment, a constitution which includes only one pair of wires and is capable of bending in two directions may be adopted. In this case, the bending section may be configured by disposing the two protrusion parts and the two receiving surfaces at the same phase around the central axis and disposing all of the basic joint rings to be arranged so that phases of the protrusion parts coincide. With such a constitution, a size in a longitudinal direction of the bendable mechanism is capable of being configured to be shortened. In addition, when the distal end side joint ring and the proximal end side joint ring are attached to be rotatable around the axis with respect to the insertion section, and the entire bendable mechanism is configured to be rotatable around the axis with respect to another place of the insertion section by an operation of the operating unit, a constitution which is capable of bending in two directions and is capable of changing a bending direction thereof to a desired direction is capable of being realized.

Moreover, the endoscope as the medical manipulator of the present invention is not limited to an endoscope having a hard insertion section. Therefore, a flexible endoscope in which a region other than the bending section in the insertion section has flexibility may be adopted. Furthermore, although a structure of the present invention exhibits significant effects when the bending section is driven using a drive mechanism such as a motor, the present invention is also applicable to a constitution in which the bending section is manually driven using a known dial knob or the like.

In addition, the end effector included in the medical manipulator of the present invention is not limited to the above-described observation section. For example, various constitutions used for treatment such as high frequency knives or the like used while receiving electricity or grasping forceps or the like used without receiving electricity may be adopted.

What is claimed is:

1. A joint ring comprising:
a main body formed in an annular shape, the main body comprising a first surface and a second surface, the first surface and the second surface intersect a central axis of the main body, the second surface is opposite to the first surface, the main body comprising:
a first hole penetrated in a direction of the central axis of the main body, the first hole having a first opening on the first surface, the first opening configured to engage with a spherical surface, and
a second hole penetrated in the direction of the central axis of the main body, the second hole having a second opening on the first surface,
a protrusion comprising a first end and a second end, the first end is spherical so that the first end can engage and slide with a mating surface of an adjacent joint ring, the second end is fixed in the second opening,
wherein:
the first hole comprising a pair of first holes formed to oppose each other across the central axis;
the second hole comprising a pair of second holes formed to oppose each other across the central axis;
the pair of first holes being offset in a circumferential direction of the main body from the pair of second holes; and
the protrusion comprising a pair of protrusions, each having the second end fixed in a respective second opening,
each protrusion comprising a third hole penetrated from the first end to the second end;
wherein the third hole extending to be parallel to the central axis, and the pair of first holes pass through the main body part parallel to the central axis,
a diameter of the third hole, in a portion of the protrusion fixed in the second hole, gradually increases toward both ends thereof in the direction of the central axis, and
diameters of the pair of first holes gradually increase toward both ends thereof in the direction of the central axis;
each second hole having at least a portion having a first cylindrical shape; and
the first end of each of the pair of protrusions has a second cylindrical shape mating with the first cylindrical shape.

2. A bending section of a medical manipulator, the bending section comprising:
a joint comprising a first joint ring and a second joint ring;
the first joint ring having a first main body formed in a first annular shape, the first joint ring comprising:
a first surface intersecting a first central axis of the first main body; and
a first hole penetrated in a direction of the first central axis of the first main body, the first hole having a first opening on the first surface, the first opening configured to engage with a spherical surface,
the second joint ring having a second main body formed in a second annular shape, the second joint ring comprising:
a second surface intersecting a second central axis of the second main body and opposing the first surface of the first joint ring; and a second hole penetrated in a direction of the second central axis of the second main body, the second hole having a second opening on the second surface; and a protrusion comprising a first end and a second end, the first end having the spherical surface configured to engage and slide with the first opening of the first hole, the second end is fixed to the second opening, wherein:

the first hole comprising a pair of first holes formed to oppose each other across the first central axis;

the second hole comprising a pair of second holes formed to oppose each other across the second central axis;

the pair of first holes being offset in a circumferential direction of the first main body from the pair of second holes; and the protrusion comprising a pair of protrusions, each having the second end fixed in a respective second opening.

3. The joint ring according to claim 2, wherein:

each protrusion comprising a third hole penetrated from the first end to the second end;

wherein the third hole extending to be parallel to the central axis, and the pair of first holes pass through the main body part parallel to the central axis.

4. The joint ring according to claim 3, wherein:

a diameter of the third hole, in a portion of the protrusion fixed in the second hole, gradually increases toward both ends thereof in the direction of the central axis, and diameters of the pair of first holes gradually increase toward both ends thereof in the direction of the central axis.

5. The joint ring according to claim 4, wherein:

each second hole having at least a portion having a first cylindrical shape; and the first end of each of the pair of protrusions has a second cylindrical shape mating with the first cylindrical shape.

6. A medical manipulator comprising:

the bending section according to claim 2; and a wire inserted in each of the first hole, the second hole, and the third hole.

* * * * *